United States Patent
Rondoni et al.

(10) Patent No.: US 7,522,061 B2
(45) Date of Patent: Apr. 21, 2009

(54) EXTERNAL VOIDING SENSOR SYSTEM

(75) Inventors: John C. Rondoni, Plymouth, MN (US); Martin T. Gerber, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 208 days.

(21) Appl. No.: 11/414,626

(22) Filed: Apr. 28, 2006

(65) Prior Publication Data
US 2007/0252714 A1 Nov. 1, 2007

(51) Int. Cl.
*G08B 23/00* (2006.01)

(52) U.S. Cl. ............. 340/573.5; 340/573.4; 340/573.6; 340/571; 604/133; 604/361; 604/362; 607/41; 607/48

(58) Field of Classification Search ............. 340/573.4, 340/573.5, 573.6, 571–604; 604/133, 361, 604/362; 607/41–48; 128/886
See application file for complete search history.

(56) References Cited

U.S. PATENT DOCUMENTS

| | | | |
|---|---|---|---|
| 4,205,671 A * | 6/1980 | Lassen | 128/886 |
| 4,760,383 A | 7/1988 | DiLorenzo | |
| 4,873,990 A | 10/1989 | Holmes et al. | |
| 4,928,690 A * | 5/1990 | Heilman et al. | 607/4 |
| RE33,360 E | 10/1990 | Reynolds et al. | |
| 4,977,906 A | 12/1990 | Di Scipio | |
| 5,103,835 A | 4/1992 | Yamada et al. | |
| 5,331,548 A | 7/1994 | Rollema et al. | |
| 5,396,897 A | 3/1995 | Jain et al. | |
| 5,416,469 A | 5/1995 | Colling | |
| 5,704,353 A | 1/1998 | Kalb et al. | |
| 5,760,694 A * | 6/1998 | Nissim et al. | 340/604 |
| 6,354,991 B1 | 3/2002 | Gross et al. | |
| 6,360,123 B1 | 3/2002 | Kimichi et al. | |
| 6,372,951 B1 * | 4/2002 | Ter-Ovanesyan et al. | 604/361 |
| 6,384,728 B1 | 5/2002 | Kanor et al. | |

(Continued)

FOREIGN PATENT DOCUMENTS

FR 2 788 430 7/2000

(Continued)

OTHER PUBLICATIONS

Martin T. Gerber, "Impedance-Based Bladder Sensing," U.S. Appl. No. 11/261,443, filed Oct. 28, 2005.

(Continued)

*Primary Examiner*—Jeffery Hofsass
*Assistant Examiner*—Sisay Yacob
(74) *Attorney, Agent, or Firm*—Shumaker & Sieffert, P.A.

(57) ABSTRACT

The disclosure describes an external sensor attached to an undergarment worn by a patient that detects voiding information. The sensor stores the voiding information in a voiding log and transmits the voiding log to an external device. The external device includes a user interface that displays the voiding log to the patient for review. The patient may correct any incorrect voiding information that was logged in error or due to a non-voiding event. A user, such as a clinician or the patient, may use the voiding information to diagnose a condition of the patient. In addition, the voiding information of the voiding log may be used by the user to adjust a stimulation therapy or the external device to automatically adjust stimulation therapy. The undergarment may be disposable or washable after patient use.

32 Claims, 11 Drawing Sheets

U.S. PATENT DOCUMENTS

| | | |
|---|---|---|
| 6,393,323 B1 | 5/2002 | Sawan et al. |
| 6,433,695 B1 | 8/2002 | Kai et al. |
| 6,440,090 B1 | 8/2002 | Schallhorn |
| 6,454,720 B1 | 9/2002 | Clerc et al. |
| 6,652,449 B1 | 11/2003 | Gross et al. |
| 6,662,052 B1 | 12/2003 | Sarwal et al. |
| 6,689,056 B1 | 2/2004 | Kilcoyne et al. |
| 6,712,772 B2 | 3/2004 | Cohen et al. |
| 6,766,817 B2 | 7/2004 | da Silva |
| 6,862,480 B2 | 3/2005 | Cohen et al. |
| 6,896,651 B2 | 5/2005 | Gross et al. |
| 6,918,404 B2 | 7/2005 | Dias da Silva |
| 7,066,586 B2 | 6/2006 | da Silva |
| 7,101,343 B2 | 9/2006 | Delalic et al. |
| 2002/0019615 A1* | 2/2002 | Roe et al. .................. 604/361 |
| 2002/0055761 A1 | 5/2002 | Mann et al. |
| 2002/0062060 A1 | 5/2002 | Gross et al. |
| 2002/0103424 A1 | 8/2002 | Swoyer et al. |
| 2002/0111586 A1 | 8/2002 | Mosel et al. |
| 2003/0009201 A1 | 1/2003 | Forsell |
| 2003/0014091 A1 | 1/2003 | Rastegar et al. |
| 2003/0100930 A1 | 5/2003 | Cohen et al. |
| 2003/0144710 A1 | 7/2003 | Haugland et al. |
| 2004/0147871 A1 | 7/2004 | Burnett |
| 2004/0152999 A1 | 8/2004 | Cohen et al. |
| 2004/0220538 A1 | 11/2004 | Panopoulos |
| 2004/0230172 A1* | 11/2004 | Shapira .................. 604/361 |
| 2005/0060001 A1 | 3/2005 | Singhal et al. |
| 2005/0065408 A1 | 3/2005 | Benderev |
| 2005/0096751 A1 | 5/2005 | Gerber et al. |
| 2005/0099294 A1* | 5/2005 | Bogner et al. ............ 340/540 |
| 2005/0177067 A1 | 8/2005 | Tracey et al. |
| 2005/0245840 A1 | 11/2005 | Christopherson et al. |
| 2005/0261746 A1 | 11/2005 | Gross et al. |
| 2005/0288603 A1 | 12/2005 | Goping |
| 2006/0004421 A1* | 1/2006 | Bennett et al. ............ 607/41 |
| 2006/0020225 A1 | 1/2006 | Gerber et al. |
| 2006/0190047 A1 | 8/2006 | Gerber et al. |
| 2006/0190048 A1 | 8/2006 | Gerber et al. |
| 2006/0190049 A1 | 8/2006 | Gerber et al. |
| 2006/0190050 A1 | 8/2006 | Gerber et al. |
| 2006/0190051 A1 | 8/2006 | Gerber et al. |
| 2006/0247723 A1 | 11/2006 | Gerber et al. |
| 2006/0247724 A1 | 11/2006 | Gerber et al. |
| 2006/0247725 A1 | 11/2006 | Gerber et al. |
| 2007/0027494 A1 | 2/2007 | Gerber |
| 2007/0027495 A1 | 2/2007 | Gerber |

FOREIGN PATENT DOCUMENTS

| | | |
|---|---|---|
| WO | WO 96/14813 | 5/1996 |
| WO | WO 98/02209 | 1/1998 |
| WO | WO 01/00117 | 1/2001 |
| WO | WO 2004/049969 | 6/2004 |

OTHER PUBLICATIONS

Coosemans et al., "Datalogger for Bladder Pressure Monitoring with Wireless Power and Data Transmission," Katholieke Universiteit Leuven, Department ESAT-MICAS, Belgium, Belgian Day on Biomedical Engineering, Oct. 17, 2003, (1 page).

Siwapornsathain et al., "A Telemetry and Sensor Platform for Ambulatory Urodynamics," Department of Electrical and Computer Engineering, University of Wisconsin—Madison, Date unknown, (5 pages).

"Wireless Physiological Pressure Transducer," Memscap Sensor Solutions, May 2003, (2 pages).

"Standardisation of Ambulatory Urodynamic Monitoring," Report of the Standardisation Sub-Committee of the ISC for Ambulatory Urodynamic Studies, Date unknown, (21 pages).

International Search Report and Written Opinion dated Jul. 26, 2007 for corresponding PCT Application No. PCT/US2007/001883, (13 pgs.).

Rondoni et al., "External Voiding Sensor System," U.S. Appl. No. 11/414,508, filed Apr. 28, 2006.

Notification of Transmittal of the International Preliminary Report on Patentability dated Aug. 19, 2008 for corresponding PCT Application Serial No. PCT/US2007/001883 (9 pgs.).

* cited by examiner

EXTERNAL VOIDING SENSOR SYSTEM

TECHNICAL FIELD

The invention relates to implantable medical devices and, more particularly, external sensors.

BACKGROUND

Urinary incontinence, or an inability to control urinary function, is a common problem afflicting people of all ages, genders, and races. Various muscles, nerves, organs and conduits within the urinary tract cooperate to collect, store and release urine. A variety of disorders may compromise urinary tract performance and contribute to incontinence. Many of the disorders may be associated with aging, injury or illness.

In some cases, urinary incontinence can be attributed to improper sphincter function, either in the internal urinary sphincter or external urinary sphincter. For example, aging can often result in weakened sphincter muscles, which causes incontinence. Some patients also may suffer from nerve disorders that prevent proper triggering and operation of the bladder or sphincter muscles. Nerves running though the pelvic floor stimulate contractility in the sphincter. A breakdown in communication between the nervous system and the urinary sphincter can result in urinary incontinence.

Monitoring urinary incontinence aids a clinician in diagnosing the precise condition of the patient. Monitoring may include a diary maintained by the patient in which the patient logs voluntary voiding events, involuntary voiding events, i.e., leakage, or other related problems. The patient may keep the diary on paper or in an electronic device. The clinician may review the diary to view the frequency and number of voiding events experienced by the patient. In some cases, the clinician may tailor a stimulation therapy according to the diary.

Electrical stimulation of nerves in the pelvic floor may provide an effective therapy for a variety of disorders, including urinary incontinence. For example, an implantable electrical stimulator may be provided. The electrical stimulator may be a neurostimulator that delivers electrical stimulation to the sacral nerve to induce sphincter constriction and thereby close or maintain closure of the urethra at the bladder neck. In addition, electrical stimulation of the bladder wall may enhance pelvic floor muscle tone and assist fluid retention in the bladder or voiding fluid from the bladder. An appropriate course of neurostimulation therapy may be aided by the diary that monitors voiding events and tracks the therapy.

SUMMARY

The disclosure is directed to an external sensor attached to an undergarment worn by a patient that detects voiding information. The sensor stores the voiding information as a voiding log locally or in a separate device. The separate device may include a user interface that displays the voiding log to the patient for review. The patient may correct voiding information that was logged in error or relates to a non-voiding event. A user, such as a clinician or the patient, may use the voiding information to diagnose a condition of the patient, such as urinary incontinence.

Maintaining an accurate voiding diary is often difficult for a patient. The patient needs to spend time to manually enter a voiding event whenever it occurs. This manual diary also can be inaccurate because entries by the patient are subjective and may be influenced by embarrassment or other issues. An external sensor, as described herein, may be beneficial in providing the patient with an objective sensing system that automatically detects voiding information and stores it in a voiding log, without the need for significant patient interaction.

In some embodiments, the external sensor is located in an undergarment worn by the patient. However, other external sensors are possible either in addition or as an alternative to a sensor in an undergarment. If an undergarment is used, it may also be disposable or washable to reduce possible contamination problems from bodily fluids that come into contact with the undergarment, such as urine. In addition to keeping a voiding log, the voiding information may be used by the user to manually adjust electrical stimulation therapy to a nerve or muscle of the patient. In addition, or in the alternative, the external device may automatically adjust the stimulation therapy after processing the voiding log.

In one embodiment, the invention provides a method comprising detecting urinary voiding information via a sensor disposed adjacent to a patient via an undergarment worn by the patient, and storing the voiding information in a voiding log.

In another embodiment, the invention provides a system comprising an undergarment for a patient, a sensor carried by the undergarment and positioned to detect urinary voiding information, and a memory that stores the voiding information in a voiding log.

In an additional embodiment, the invention provides a system comprising an implantable stimulator that delivers electrical stimulation therapy to a patient to alleviate urinary incontinence, an undergarment for the patient, a sensor carried by the undergarment and positioned to detect urinary voiding information, an external programmer that controls the implantable stimulator and receives the voiding information from the sensor, wherein the programmer stores the voiding information in a voiding log.

In various embodiments, the invention may provide one or more advantages. For example, the patient may discreetly wear an undergarment that includes a sensor to automatically generate a voiding log based on detected voiding information. This may allow the patient to eliminate the need to keep a manual voiding diary. The undergarment may be disposable or washable to maintain a healthy detection environment. The system also allows the patient or clinician to review the voiding log and make changes to incorrect voiding information. The sensor may also be used as feedback for manual or automatic adjustment of electrical stimulation therapy delivered to the patient for urinary incontinence.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
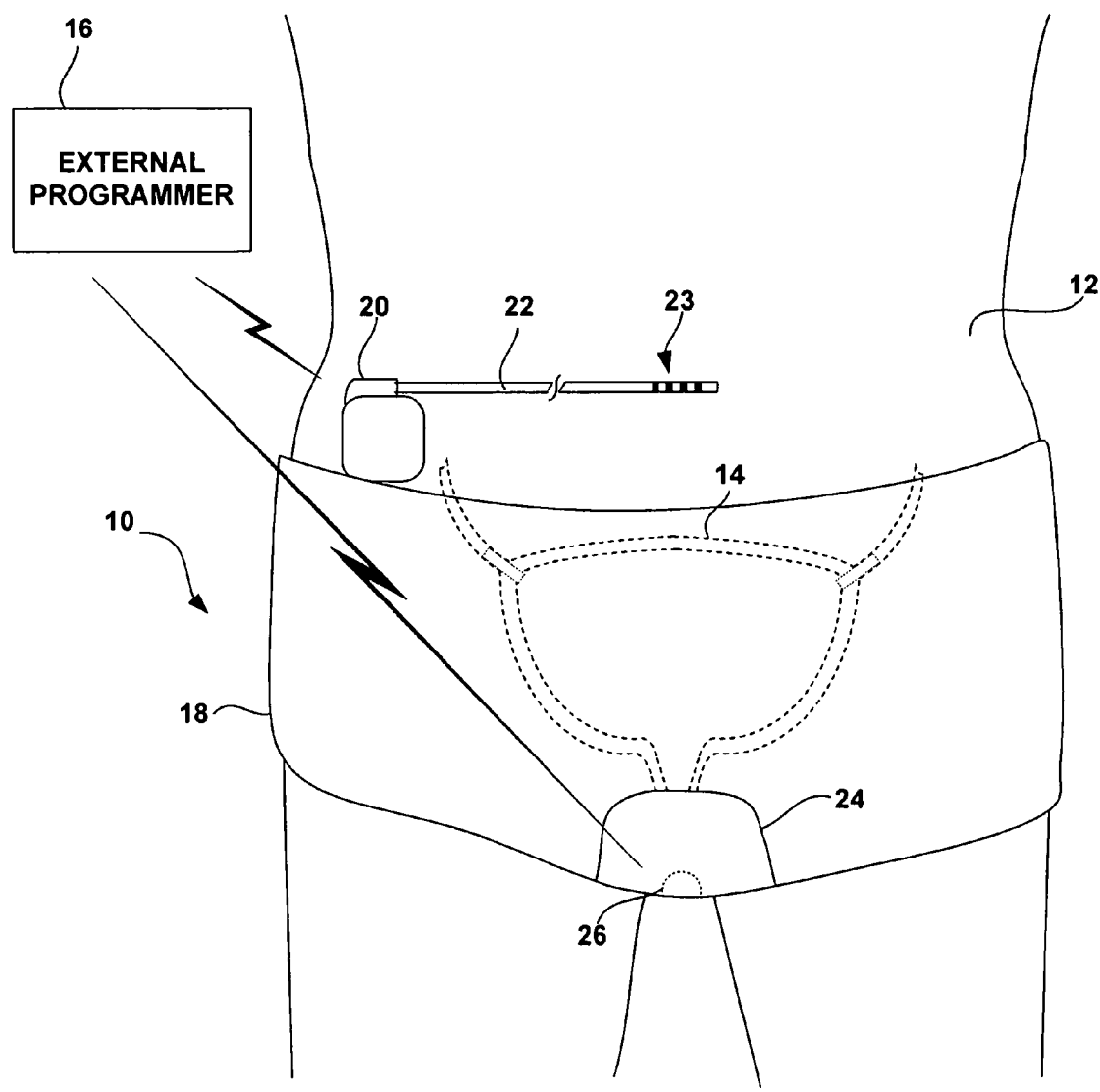
FIG. 1 is a schematic diagram illustrating an implantable stimulation system, incorporating a sensor in an undergarment to detect voiding information.

Urinary incontinence is a condition that affects the quality of life and health of many people. Tracking urinary voiding events may be important in quantifying the number of voluntary or involuntary events a patient has every day or qualifying the severity of the urinary incontinence condition. In accordance with this disclosure, a sensor is located outside of a patient to detect voiding information from the patient. The voiding information may be stored in a voiding log, and the voiding log may be reviewed by a clinician or the patient. The voiding log may eliminate the need for a patient to manually track voiding events, such as urine leakage or complete voluntary or involuntary voids.

Manually tracking voiding events, e.g. keeping a voiding diary, is often undesirable for the patient. Keeping the voiding diary takes time out of the patient's day and may be noticed by other people, causing embarrassment to the patient. In addition, manually tracking voiding events may result in voiding information errors. For example, the patient may inadvertently forget to record an event, fail to objectively describe the event, or even purposefully keep false voiding information in the diary. These problems with a voiding diary may undermine the ability of the clinician to properly assess patient condition and prescribe an effective therapy.

As described herein, the patient may wear an undergarment that includes an attached sensor that detects voiding information and saves the voiding information in a voiding log. The sensor may record and transmit a voiding log to an external device, e.g., an external programmer. Alternatively, the sensor may transmit voiding information to the external device, which then records and maintains the voiding log. In either case, the voiding log allows the clinician or the patient to review the voiding log and address the condition of the patient. The programmer may allow the patient or clinician to correct or remove voiding information that is incorrect. For example, the sensor may incorrectly indicate a voiding event based on detected wetness from a drink spilled on the patient's legs.

In addition, the voiding log may be used in conjunction with stimulation therapy. The patient or clinician may review the voiding information of the voiding log to manually adjust one or more stimulation parameters of the therapy. Alternatively, the external device, e.g., programmer, may process the voiding information and automatically adjust one or more stimulation parameters to increase the efficacy of the stimulation therapy. For example, if leakage frequency increases, the patient, clinician or programmer may increase the intensity of electrical stimulation to prevent or reduce involuntary voiding.

An external sensor described herein may also be used to correlate external voiding data with internal sensor data to indicate which internal data is indicative of a voiding event. In this manner, the internal sensor may be trained to recognize voiding events based upon the voiding information from the external sensor. This system may reduce or eliminate the need to receive input from the patient or a clinician to calibrate an implanted feedback system.

While the sensor described herein is attached to an undergarment worn by the patient, the sensor may be located on the outside of the patient in a different manner. For example, the sensor may be adhered to skin of the patient by an adhesive or tape, the sensor may be sutured to the skin of the patient, or the sensor may be strapped to the patient via a strap or cable. In other embodiments, the sensor may be sewn or adhered to another article of clothing worn by the patient or the sensor may be attached to a material which is placed between clothing and the skin of the patient.

FIG. 1 is a schematic diagram illustrating an implantable stimulation system 10, incorporating a sensor in an undergarment to detect voiding information. As shown in FIG. 1, system 10 includes stimulator 20, external programmer 16, and undergarment 18. Undergarment 18 includes absorbent pad 24 that holds sensor 26 near the opening of the patient's urethra (not shown). Sensor 26 transmits voiding information to external programmer 16 when the sensor detects moisture or when the external programmer requests the voiding information. The voiding information is stored in a voiding log, where the voiding log is stored in a memory of sensor 26, programmer 16, or both.

Patient 12 wears undergarment 18 between regular articles of clothing and the skin of the patient so that sensor 26 may detect voiding information. Voiding information may include complete voiding events, urinary leakage, or other wetness events from urine exiting bladder 14. Sensor 26 detects the presence of fluid which indicates that voiding has occurred. Sensor 26 may determine wetness by detecting a decrease in resistance between two electrodes of the sensor. In some cases, sensor 26 may be capable of also detecting fluid pH, impedance, electrolyte concentration, or other characteristics of the fluid to identify that the fluid is urine.

Sensor 26 may be located on an external surface of absorbent pad 24 or within the absorbent pad. Absorbent pad 24 may be constructed of cotton, cellulose, or a hydro-gel. As patient 12 voids urine, absorbent pad 24 holds the urine by allowing the urine to spread out in the pad. When the urine reaches sensor 26, the sensor detects the wetness as voiding information and stores the voiding information in a voiding log, either locally or in external programmer 16. Absorbent pad 24 may be capable of retaining an ounce of fluid or greater than 20 ounces of fluid, depending on the material used to construct the absorbent pad.

Sensor 26 may transmit voiding information to external programmer 16 as pre-determined by the factory or the clinician. In some embodiments, sensor 26 may transmit voiding information any time that the sensor detects voiding information and a connection with programmer 16 can be established. In other embodiments, if sensor 26 locally stores a voiding log, sensor 26 may transmit voiding information when the sensor can no longer store more voiding information in the voiding log. Alternatively, sensor 26 may transmit voiding information at any time the information is requested by external programmer 16. Patient 12 or the clinician may interact with external programmer 16 and cause the programmer to request the voiding log from sensor 26.

Patient 12 or the clinician may enter a review program of external programmer 16 to view each component of the voiding information contained in the voiding log. A component may be one voiding event detected by sensor 26. External programmer 16 may allow patient 12 or the clinician to modify a component of the voiding log to correct any incorrect voiding information. During normal operation, sensor 26 may detect voiding information that is not an actual voiding event, otherwise known as a false positive. False positives may be produced by activities or situations in which patient 12 participates during normal living. Exemplary false positives may include sweating during an aerobic activity, spilling a glass of liquid on the lap of patient 12, or any other time when urine is not the source of the voiding information detection.

In some embodiments, sensor 26 may detect other characteristics of the fluid to identify the fluid as urine in order to reduce any false positive detection. In addition, sensor 26 may be configured to sense an amount of fluid associated with a voiding event. Hence, the voiding information may include a variety of information including a voiding event indication, the date and time of the voiding event, an amount of fluid discharged in association with the voiding event, and/or physical characteristics of the fluid.

Although external programmer 16 is generally described as a programmer in contemplation its combined role in storing and presenting a voiding diary, and controlling an implantable stimulator 20, it may alternatively be configured only as a voiding diary recording device. For example, an external voiding diary logging device may be provided in addition to a separate external programmer for an implanted electrical stimulation device. Alternatively, an external voiding diary logging device may be used in combination with sensor 26 prior to implantation of stimulator 20, e.g., for study of the patient's condition to determine whether implantation is advisable.

Stimulator 16 at least partially prevents unwanted urinary voiding events by electrically stimulating a pelvic floor nerve, a pelvic floor muscle, or the urinary sphincter. Examples of a pelvic floor nerve include the pudendal nerve, the sacral nerve, or nerves of the sacral plexus. Stimulator 16 includes a pulse generator that generates electrical pulses and delivers the electrical pulses to a target tissue, e.g., the urinary sphincter, via lead 22 and one or more electrodes 23 located at the distal end of the lead. After reviewing the voiding log, the clinician or patient 12 may use the information to adjust one or more stimulation parameters that define the stimulation therapy provided by stimulation 20 via lead 22. The clinician interacts with external programmer 16 to adjust the stimulation therapy to reduce the frequency or number of voiding events identified in the voiding log.

In some embodiments, stimulator 20 uses multiple programs to deliver stimulation therapy, wherein one program includes a set of stimulation parameters. The clinician may change each of the programs, or only the programs used during the time when the voiding information was detected. Example stimulation parameters include an electrode configuration, a pulse rate, a pulse width, and voltage amplitude or current amplitude. Electrode configuration may refer to both a combination of selected electrodes and polarities of the electrodes, i.e., as cathode or anode.

In other embodiments, external programmer 16 may automatically analyze the voiding log, e.g., for leakage frequency or other characteristics, and automatically make adjustments to one or more stimulation parameters. External programmer 16 may include instructions that identify which parameters to adjust when a certain type of voiding information is detected. Alternatively, external programmer 16 may provide suggested adjustments to the clinician or patient 12, and the adjustments may not take effect until the clinician or the patient agrees with the suggestion.

Because undergarment 18 and, more specifically, absorbent pad 24 may come into contact with urine or other bodily fluids, the undergarment may be either disposable or washable. If undergarment 18 is disposable, patient 12 may discard the undergarment and everything attached as refuse. Patient 12 may use a new undergarment 18 if a voiding log is still to be stored. If undergarment 18 is washable, patient 12 may reuse the undergarment after the undergarment is cleaned to remove any urine or other bodily fluids. In either case, sensor 26 may stay with undergarment 18, but patient 12 may need to remember to transmit the voiding log from the sensor to external programmer 16 prior to disposal to prevent risk of loss of detected voiding information.

While stimulation 20 is described in FIG. 1, in conjunction with external programmer 16, other embodiments of system 10 do not include stimulation 20 or any other stimulation therapy device. In these embodiments, sensor 26 is used primarily as a diagnostic tool to provide objective patient 12 condition information for the clinician. The clinician may use the voiding log to determine an appropriate course of treatment, which may or may not include stimulation therapy. In this case, the voiding log is stored locally in memory associated with sensor 26, or stored in an external voiding diary logging device, as mentioned above.

In alternative embodiments of system 10, sensor 26 may not be included in undergarment 18. For example, sensor 26 may be included in a separate absorbent pad that fits in patient 12 underwear to maximize patient comfort. The pad may be gender specific, with sensor 26 located near the middle for female anatomy and near the anterior side for male anatomy. In addition, sensor 26 may also be located at the distal tip of a condom-like device that males may use to cover the penis. Other embodiments may also include sensor 26 taped to the skin of patient 12, trapped between clothing and the skin, attached to the inside of other clothing, sutured to the skin of the patient, or held to the skin of the patient via a strap.

Figure 2:
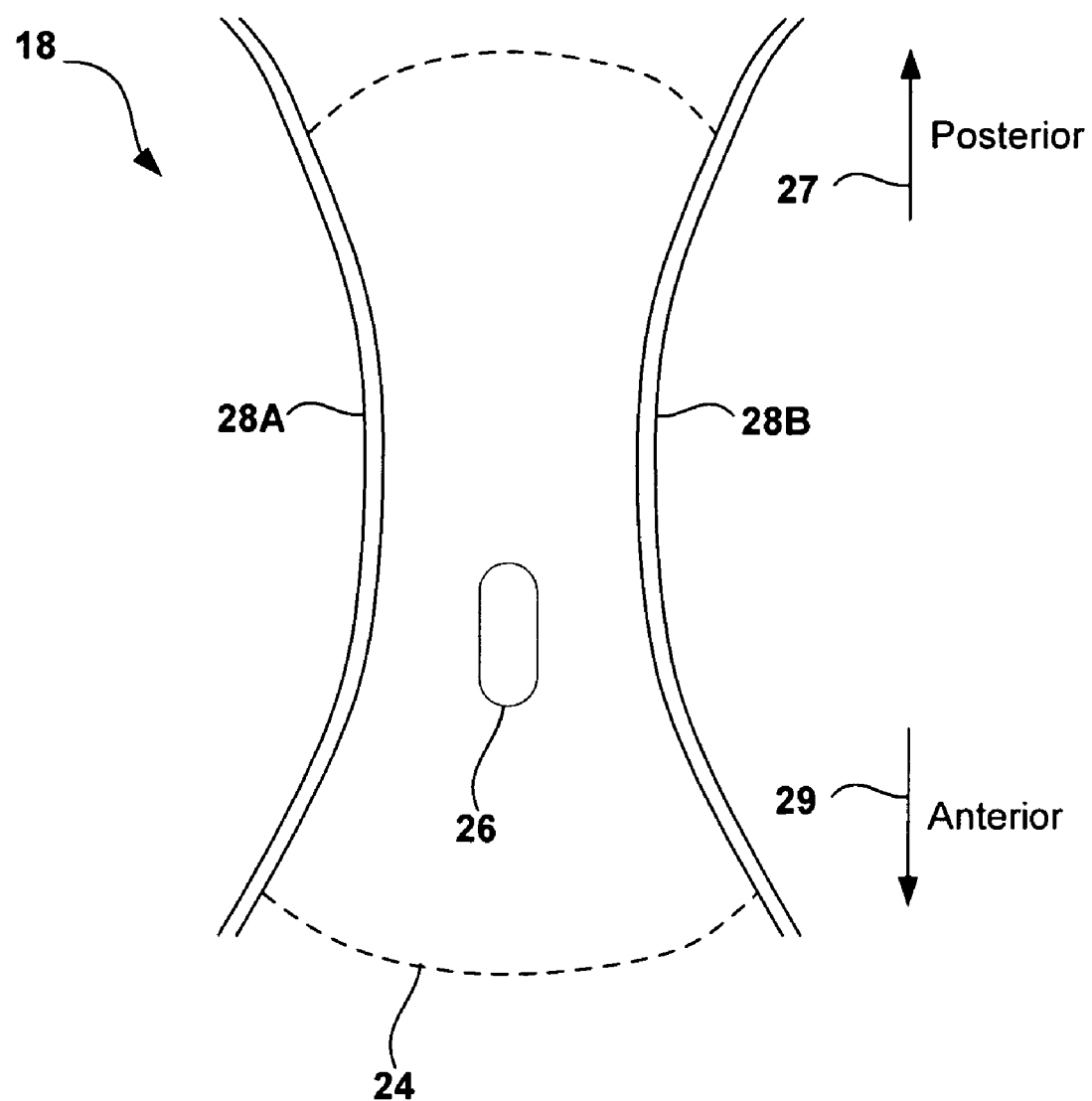
FIG. 2 is a schematic diagram illustrating an absorbable pad of an undergarment with a sensor attached to an external surface of the pad.

FIG. 2 is a schematic diagram illustrating an absorbable pad of an undergarment with a sensor attached to an external surface of the pad. As shown in FIG. 2, an external surface of undergarment 18 that faces the skin of patient 12 includes absorbent pad 24 and sensor 26. Undergarment 18 also includes elastic bands 28A and 28B (collectively 'elastic bands 28') which help to retain any voided urine from leaking out from the sides of undergarment 18.

Absorbent pad 24 is shaped to catch and retain any urine that is voided from patient 12. Generally, the shape of absorbent pad 24 allows at least a portion of the absorbent pad to be placed adjacent to the opening of the urethra in either a male or female patient 12. Absorbent pad 24 allows the urine to spread throughout the pad, which distributes the fluid in the pad and attempts to reduce the amount of wetness against the skin of patient 12. In some embodiments, absorbent pad 24 may distribute fluid such that all sensors 26 come into contact with a portion of the fluid. As mentioned above, absorbent pad 24 may be constructed of cotton, cellulose, a hydro-gel, some other hydrophilic material that retains urine.

The absorbent nature of absorbent pad 24 also allows sensor 26 to be placed away from the exact location that urine exits patient 12. The urine will spread through absorbent pad 24 and reach a centrally located sensor 26, such that the sensor may detect the voiding information and create an accurate voiding log from the voiding information. In the example of FIG. 2, sensor 26 is positioned slightly to the anterior, or front, location of absorbent pad 24 which is indicated by the direction of arrow 29. In gender specific undergarments 18, sensor 26 may be moved in the anterior direction for males and the sensor may be moved in the posterior direction according to arrow 27 for females.

While sensor 26 is generally oval shaped in the example of FIG. 2, the sensor may be constructed in a number of different shapes. Sensor 26 may be constructed as a flexible flat rectangle, a rigid curved shell, a sphere, a rounded and flat triangle, or any other shape capable of housing the components of sensor 26. In alternative embodiments, undergarment 18 may contain a plurality of sensors 26 arranged throughout absorbent pad 24. The plurality of sensors may each transmit data to external programmer 16 or connect to each other and transmit data together as one larger sensor. In some embodiments, multiple sensors 26 may be connected by wires to enable communication between each sensor. It may be desirable to reduce the number of wires used to connect the sensors, such as only one wire.

Figure 3:
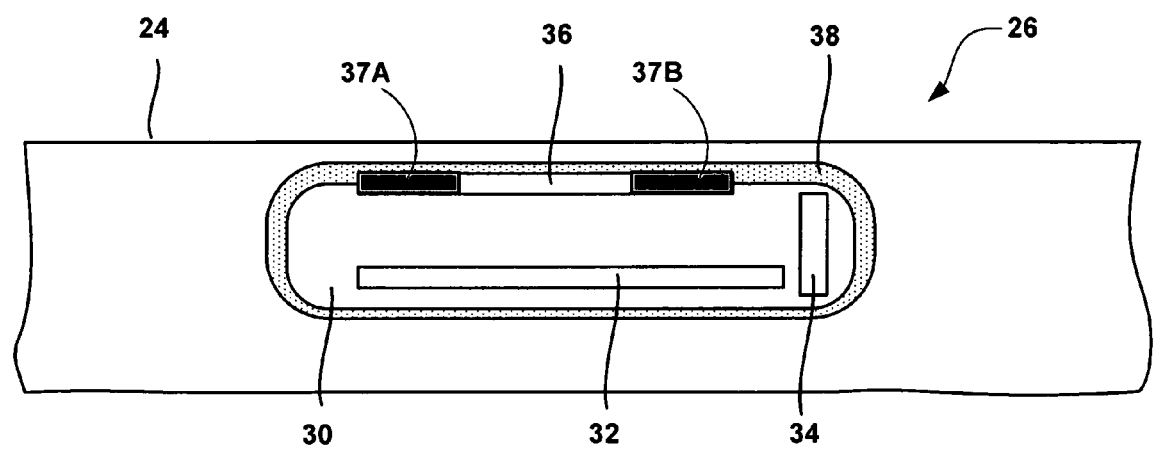
FIG. 3 is a cross-section of a sensor disposed within an absorbable pad of an undergarment.

FIG. 3 is a cross-section of a sensor 26 disposed within an absorbable pad of an undergarment. As shown in FIG. 3, sensor 26 is secured by absorbent pad 24. Sensor housing 30 of sensor 26 is embedded in absorbent pad 24, e.g., between layers of the pad. In the example of FIG. 3, sensor 26 includes circuit board 32, power source 34, and sensing element 36. Sensor housing 30 may be in the shape of a rounded capsule, as shown in FIG. 3, and includes a smooth surface. Sensing element 36 extends from housing 30. Sensing element 26 may detect a change in impedance, e.g., between two or more electrodes 37A, 37B. In this manner, sensing element 36 detects voiding information from a fluid present in absorbent pad 24. In other embodiments, sensing element 36 may include a strain gauge to detect pressure, which slightly protrudes from the housing to sense deformation changes in absorbent pad 24.

Sensor 26 rests in cavity 38 formed within absorbent pad 24. Cavity 38 may be formed between upper and lower layers of absorbent pad 24 or formed as a hollowed out region of a bed of fibers within the absorbent pad. In some embodiments, sensor 26 may have a capsule-like shape, and may have a length of approximately 2 to 10 mm, a width of approximately 2 to 5 mm, and a thickness of approximately 1 to 5 mm. The capsule-like shape may produce a circular or oval-like cross-section, in which case sensor 26 may have a diameter or major diameter of approximately 1 to 5 mm, rather than width and height dimensions. However, a capsule-like shape is merely described for purposes of example.

Sensing element 36 senses an impedance change in the space around sensor 26 from fluid within absorbent pad 24 as urine is voided from bladder 14. Sensing element 36 may detect electrical differentials, or other detectable parameters of the fluid. In some embodiments, fluid characteristics such as pH or electrolyte concentration may also be detected using pH or other chemical sensors. Processing electronics on circuit board 32 detect changes sensed by sensing element 36. Circuit board 32 communicates the voiding information to external programmer 16 by wireless telemetry. Circuit board 32 also controls the operation of sensor 26.

Embedding sensor 26 within absorbent pad 24 may be a simple method for securing the sensor 26. As bladder 14 voids urine, sensing element 36 detects a fluid within absorbent pad 24 and indicates that voiding has occurred. For example, a decrease in impedance of absorbent pad 24 may indicate that a fluid is present to more easily conduct the electrical current between two electrodes of sensing element 36. Although sensing element 36 may include electrodes, many other types of sensing components may be used to sense voiding, such as a strain gauge that measures deformation of absorbent pad 24, which indicates that the pad is swelling with urine.

Sensor 26 may have a biocompatible housing, which may be formed from titanium, stainless steel or other materials that resist corrosion. In some embodiments, sensor 26 may carry one or more expandable elements that help to anchor the sensor within absorbent pad 24. The expandable elements may be constructed from a hydrogel material. In the hydrated state, the expandable elements have a larger perimeter and may interact with the surround material of absorbent pad 24. Expansion of the expandable elements resists migration of the sensor 26 within absorbent pad 24. When allowed to dry, sensor 26 may be securely embedded within absorbent pad 24.

Figure 4:
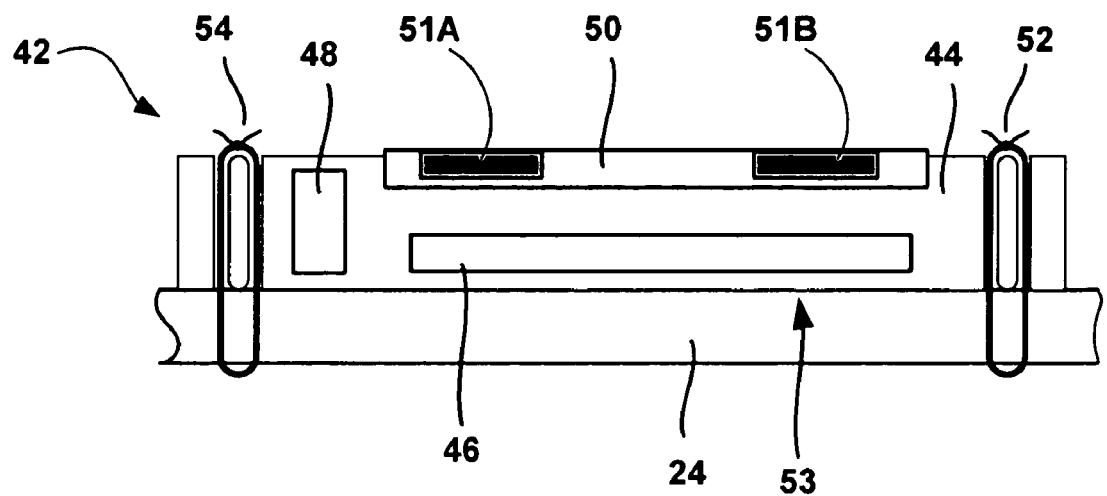
FIG. 4 is an enlarged schematic diagram illustrating a sensor sewn to an absorbent pad of an undergarment.

FIG. 4 is an enlarged schematic diagram illustrating a sensor sewn to an absorbent pad of an undergarment. Sensor 42 represents another exemplary embodiment of a sensor deployed within a patient's undergarment to detect voiding events. Sensor 42 is sutured, i.e., sewn, to absorbent pad 24, or in some cases, directly to undergarment 18 or another article of clothing. Sensor housing 44 is attached to absorbent pad 24 and includes circuit board 46, power source 48, and sensing element 50. Sutures 52 and 54 are used to attach bladder sensor 42 to absorbent pad 24. Although only two sets of sutures can be shown in FIG. 4, sensor 42 may include four or more sets, one at each corner of the rectangular shaped sensor.

Circuit board 46, power source 48 and sensing element 50 may all be similar to circuit board 32, power source 34 and sensing element 36 of FIG. 3. In addition, sensor housing 44 may be functionally similar to sensor housing 30 of FIG. 3. Differences between these components of each embodiment may relate to only the size or shape of each component. As in some embodiments of sensing element 36, sensing element 50 may include two or more electrodes 51A, 51B that detect a change in impedance of absorbent pad 24 as absorbent pad 24 swells with fluid. Sensing element 50 sends the voiding information to circuit board 46. Circuit board 46 wirelessly communicates the voiding information to external programmer 16. Circuit board 46 also may control the operation of sensor 42.

Once sensor 42 is placed on the external surface absorbent pad 24, the operator uses sutures to tie sensor 42 to absorbent pad 24, which is illustrated by sutures 52 and 54 in FIG. 4. The sutures may or may not penetrate through absorbent pad 24, and no urine will escape absorbent pad 24 in either case. In some embodiments, metal or plastic staples may be used to fix sensor 42 to absorbent pad 24 instead of nylon sutures. In some embodiments, multiple sensors 42 may be placed around absorbent pad 24 to generate an average expansion or contraction of the entire bladder.

Once attached to absorbent pad 24, sensing element 50 may be securely forced against absorbent pad 24. As absorbent pad 24 expands and contracts, sensing element 50 may sense the changed pressure by absorbent pad 24 and indicate a change in size of the pad. Similar to sensing element 36 of FIG. 3, many other types of sensing components may be used to detect voiding information of patient 12. However, electrodes that detect a change in impedance are described herein for purposes of illustration.

As an example of another fixation mechanism, sensor 42 may be provided with an adhesive backing on its underside 53 for permanent or removable attachment to absorbent pad 24 or undergarment 18. As a further alternative, the underside 53 may carry one half of a reciprocal hook-and-loop fastening device. The pad 24 or undergarment 18 may carry the other half of the hook-and-loop fastening device, which may be sewn or adhesively attached to the pad or undergarment. In this manner, sensor 42 may be removably attached to pad 24 or undergarment 18 via the hook-and-look attachment. A hook-and-loop fastener device, such as a Velcro® device, may be used. Other examples of removable attachment devices include snap-fit fasteners, press-fit fasteners or the like. Removable attachment devices may permit sensors 42 to be reused, e.g., by removing and reattaching the sensor to the different undergarments or pads, or to the same undergarment or pads between washing.

Figure 5:
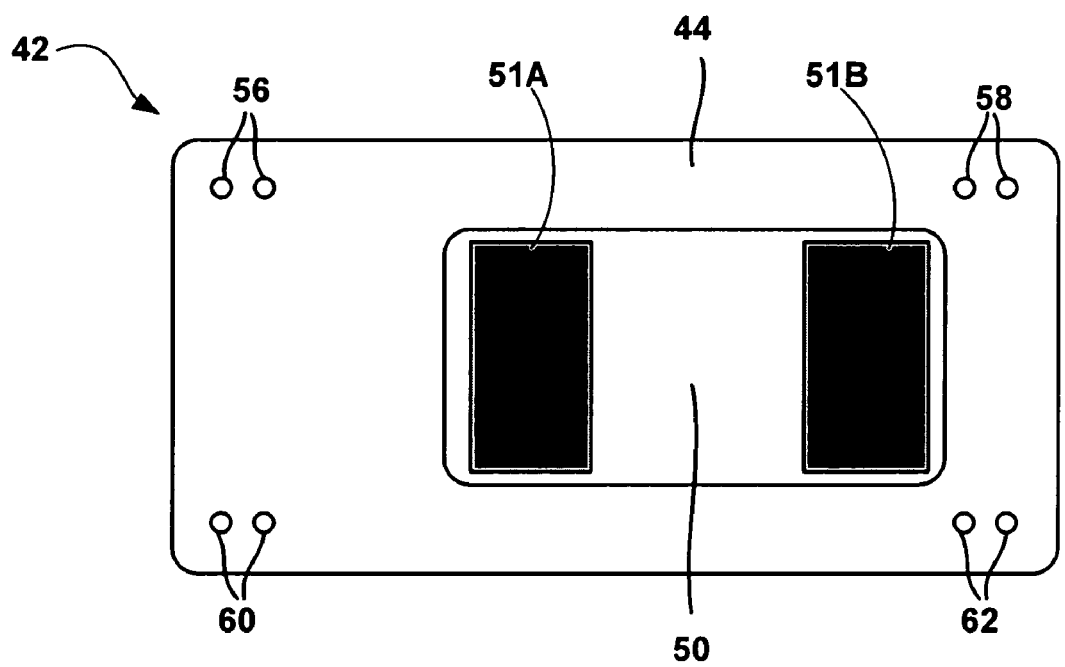
FIG. 5 is an enlarged, bottom view of the sensor of FIG. 4.

FIG. 5 is an enlarged, top view of the sensor of FIG. 4. Sensor 42 includes sensor housing 44 and sensing element 50. Fixation holes 56, 58, 60 and 62 are voids in housing 44 and allow suture to be passed through housing 44 in order for sensor 42 to be attached to absorbent pad 24. Sensing element 50 may occupy a majority of the surface area of bladder sensor 42 that faces patient 12. While sensing element 50 is rectangular in shape, the electrodes may be formed of any symmetric or asymmetrical shape, preferably circular in shape. Sensor 42 may have a length of approximately 2 to 15 mm, a width of approximately 2 to 10 mm, and a thickness of approximately 2 to 10 mm.

Fixation holes 56, 58, 60 and 62 each contain a pair of passages through housing 44. Each pair of passages is located near a corner of housing 44. An operator may pass a suture through these holes to attach housing 44 to absorbent pad 24 in a desired location of absorbent pad 24. While fixation holes 56, 58, 60 and 62 each contain two holes, other embodiments may include more or less holes in housing 44. For example, each corner of housing 44 may only contain one hole. Thread would then pass through the hole and around the outside of housing 44. As a further example, each corner may contain three holes for further securing housing 44 to absorbent pad 24.

Other fixation methods to secure bladder sensor 42 to absorbent pad 24 may include other structures different than sutures. For example, each corner of housing 44 may contain a barbed needle or helical screw that ejects from housing 44 into absorbent pad 24. The barbed needles may secure sensor 42 to absorbent pad 24 without lengthy attachment procedures. Also, as mentioned above, adhesives or hook-and-loop fasteners may be used as an alternative, or in addition to, mechanical fasteners such as staples, needles or screws. In alternative embodiments, sensor 42 is attached to the side of absorbent pad 24 facing away from patient 12. In this case, sensing element 50 would contact a surface of absorbent pad 24 to detect the voiding information.

Figure 6:
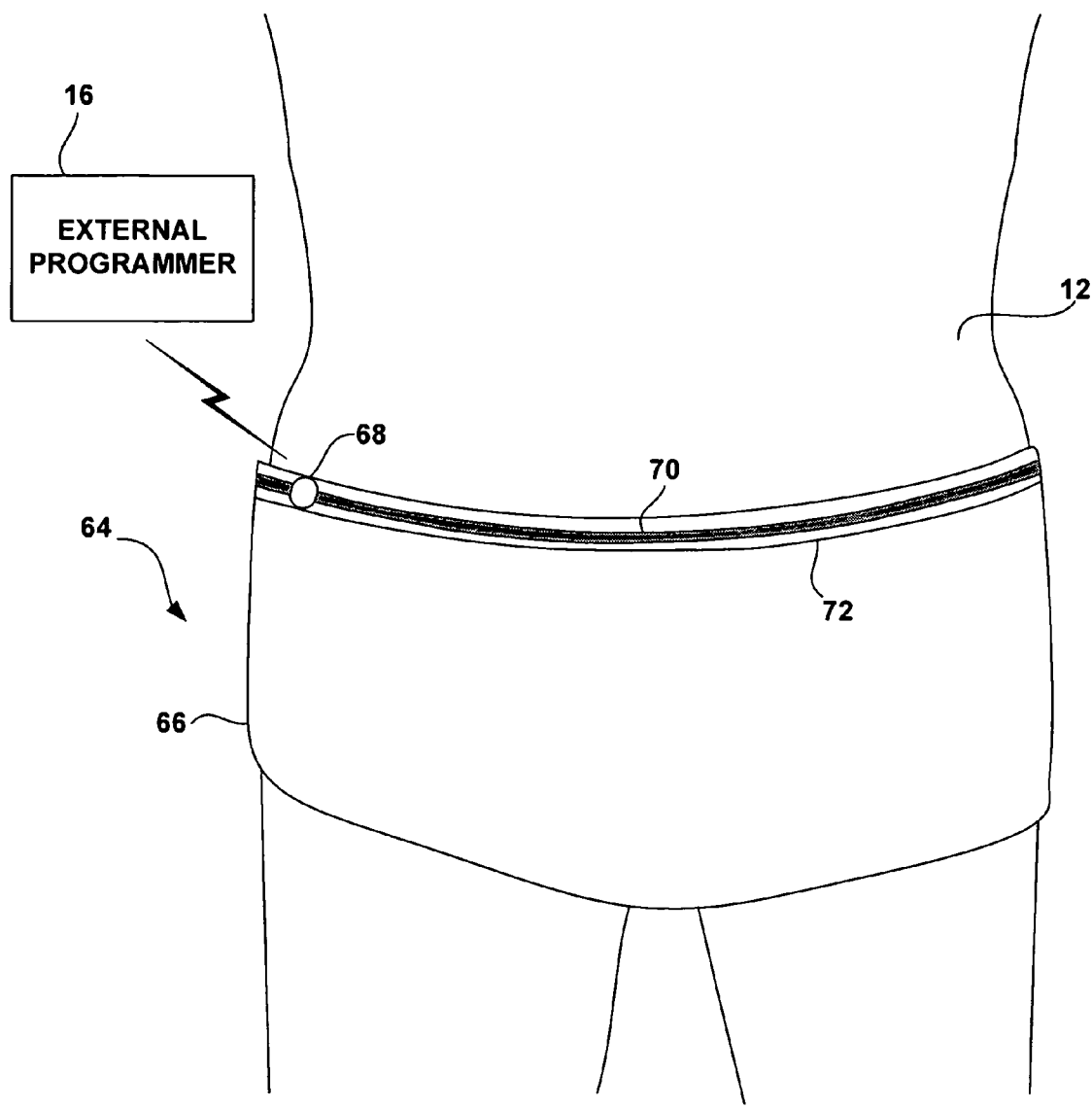
FIG. 6 is a schematic diagram illustrating a wearable undergarment, incorporating a deformation sensor to detect when the undergarment is removed.

FIG. 6 is a schematic diagram illustrating a wearable undergarment, incorporating a deformation sensor to detect when the undergarment is removed. As shown in FIG. 6, system 64 includes external programmer 16, undergarment 66, and deformation sensor 68. System 64 may be used in conjunction with system 10 to provide more complete voiding information. Sensor 68 is attached to elastic band 70, where the elastic band is disposed within waistline channel 72 of undergarment 66. Sensor 68 detects anytime that elastic band 70 is lengthened, which indicates that patient 12 is removing undergarment 66 to void bladder 14, e.g. voiding information.

Since sensor 26 of system 10 (FIG. 1) can only detect voiding information that is in the form of urine contacting undergarment 18, the voiding log may be incomplete. The voiding log of system 10 does not include voiding events that occurred when patient 12 used a toilet or other receptacle to voluntarily void urine from bladder 14. Sensor 68 may allow external programmer 16 to obtain a more complete voiding log by including all possible voiding events.

When patient 12 removes undergarment 66, the patient generally places one hand on each side of the undergarment, pulls the top of the undergarment slightly away from the skin of the patient, and lowers the undergarment from the pelvis. During this action, elastic band 70 stretches around the entire circumference of the band. Deformation sensor 68 is attached to one or both ends of elastic band 70 and transfers the force caused by stretching the elastic band into an electrical signal indicating that undergarment 66 is being removed.

The electrical signal detected by deformation sensor 68 may need to be greater than a pre-defined threshold to be considered indicative of undergarment 66 being removed. Patient 12 or the clinician may set the threshold based upon the signal from sensor 68 normally produced when the patient wears undergarment 66 and elastic band 70 encircles the patient's waist. In some cases, the threshold may be crossed for a certain period of time before sensor 68 indicates the event as a removal event. For example, a signal lasting for two seconds may be indicative of undergarment 66 being removed, in contrast to a signal lasting for one second as patient 12 adjusts undergarment 66 during the wear period.

Deformation sensor 68 may operate similar to sensor 26 when transmitting voiding information to external programmer 24. Deformation sensor 68 may transmit voiding information directly to external programmer 24 anytime a removal is detected, when a locally stored voiding log is full, or upon request from the external programmer. In embodiments combining systems 10 and 64, external programmer 24 may combine voiding information from sensors 26 and 68 into one comprehensive voiding log.

Figure 7:
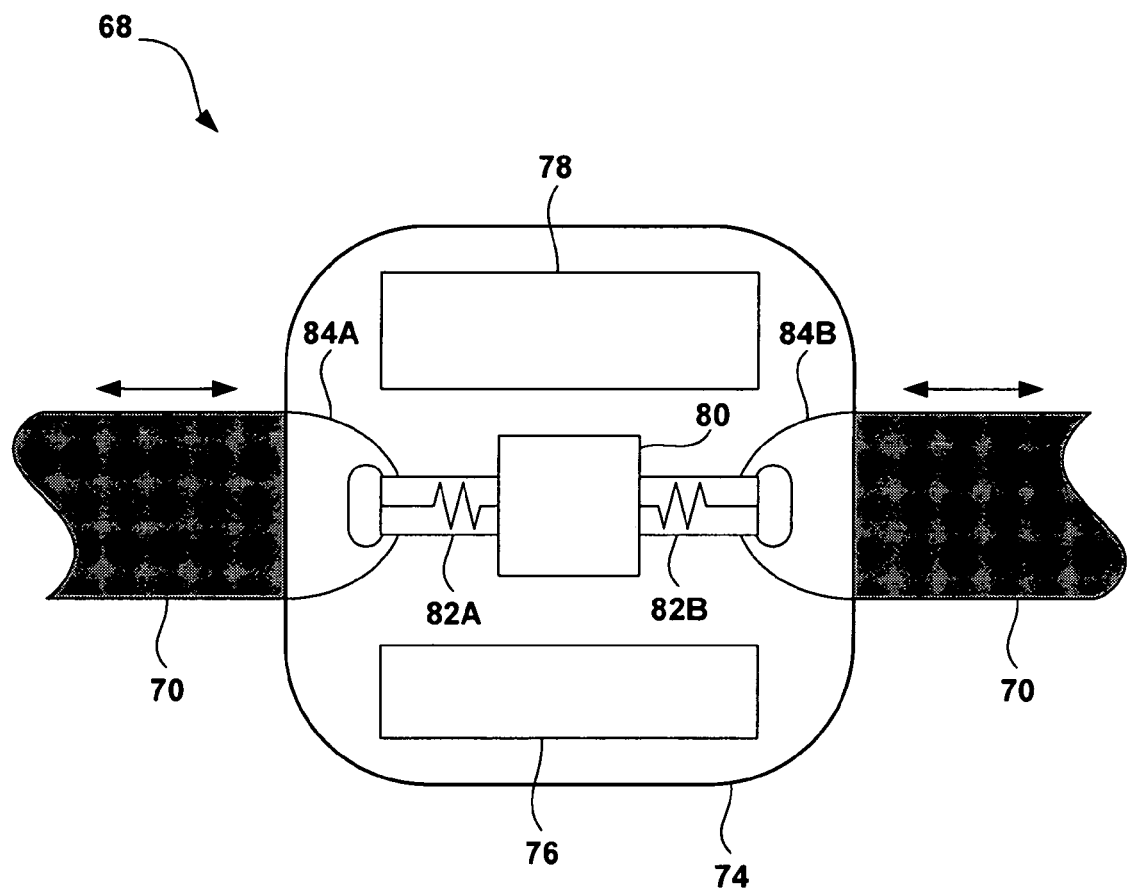
FIG. 7 is an enlarged cross-sectional side view of the deformation sensor of FIG. 6.

FIG. 7 is an enlarged cross-sectional side view of the deformation sensor of FIG. 6. As shown in FIG. 7, deformation sensor 68 includes housing 74, circuit board 76, power supply 78, sensing element 80, and resistive devices 82A and 82B (collectively "resistive devices 82). Resistive devices 82 are coupled to respective connectors 84A and 84B which are located at each end of elastic band 70. Deformation sensor 68 senses elastic band 70 stretch via resistive devices 82 and detects the voiding information at sensing element 80. Deformable sensor 68 may be located on an outside surface of undergarment 66 or within the material of the undergarment.

When elastic band 70 stretches, the resistance of resistive devices 82 changes according to the magnitude of the stretch. Sensing element 80 detects the stretch and determines if the electrical signals from resistive devices 82 are greater than the pre-defined threshold stored in a memory of circuit board 76. If the electrical signals are greater than the threshold, sensing element 80 may also sense the amount of time that the electrical signals are greater than the threshold. If the pre-defined time is exceeded, sensing element 80 may send the voiding information to circuit board 76 for transmission to external programmer 16.

In some embodiments, elastic band 70 may not be compliant. Instead band 70 may be substantially rigid. In any case, sensing element 80 may detect when the force on elastic band 70 increases. In other embodiments, deformation sensor 68 may not utilize resistive devices 82 to detect the voiding information. Instead, sensor 68 may employ strain gauge attached to elastic band 70, a rotating spool that detects removal of undergarment 66 when the spool rotates, or any other detection mechanism.

Figure 8:
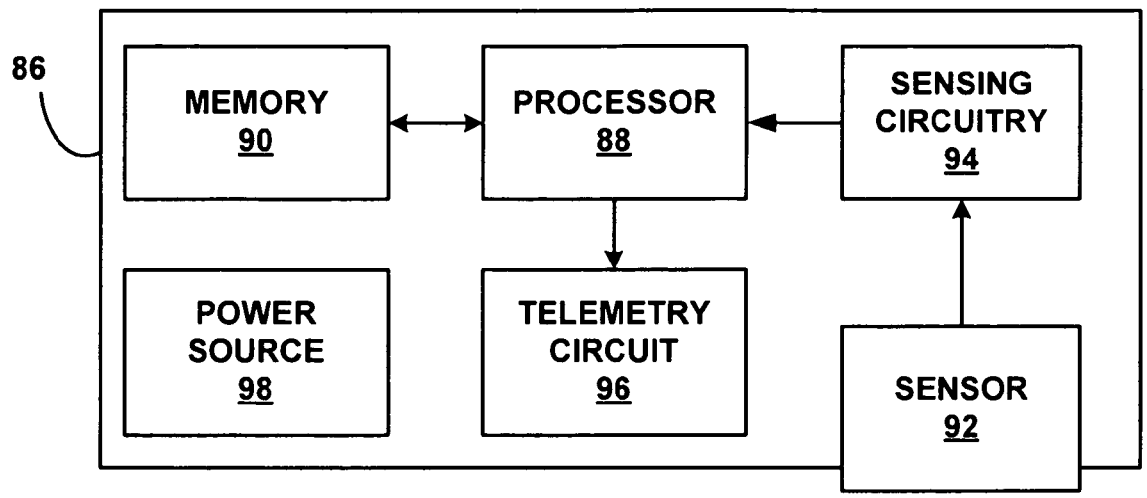
FIG. 8 is a functional block diagram illustrating various components of an exemplary sensor.

FIG. 8 is a functional block diagram illustrating various components of an exemplary sensor. As shown in FIG. 8, bladder sensors 26, 42 and 68, described herein as sensor 86. Sensor 92 may still be as describe previously with respect to each sensor. In the example of FIG. 8, sensor 86 includes a processor 88, memory 90, sensing circuitry 94, telemetry circuit 96, power source 98 and sensor 92. Sensing circuitry 94 may be carried on a circuit board, along with processor 88, memory 90 and telemetry circuit 96.

Sensor 92 may be any sensor such as a pressure sensor, impedance sensor, wetness sensor, pH sensor, deformation sensor, or any other sensor that transforms mechanical, chemical or electrical conditions into electrical signals representative of voiding information. The electrical signals may be amplified, filtered, and otherwise processed as appropriate by sensing circuitry 94 within sensor 86. In some embodiments, the signals may be converted to digital values and processed by processor 88 before being saved to memory 90 in the voiding log or sent to external programmer 16 via telemetry circuit 96.

Memory 90 stores instructions for execution by processor 88 and voiding information detected by sensing circuitry 94. Voiding information in the voiding log may then be sent to external programmer 16 for long-term storage and retrieval by a user. Memory 90 may include separate memories for storing instructions and voiding information. In some embodiments, processor 88 and memory 90 may implement loop recorder functionality in which processor 88 overwrites the oldest contents within the voiding log of the memory with new voiding information as storage limits are met, thereby conserving data storage resources within sensor 86. Alternatively, sensor 86 may be configured to immediately transmit sensed information to another device such as external programmer 16, in which case memory, processing overhead, and power consumption in sensor 86 can be substantially reduced.

Processor 88 controls telemetry circuit 96 to send voiding information to external programmer 16 on a continuous basis, at periodic intervals, or upon request from the programmer. The voiding information may be a pre-processed indication of a voiding event, in the case that sensor 86 includes the processing intelligence to analyze the sensed signals for voiding information. Alternatively, the voiding information may be raw sensor data obtained by sensor 86. In this case external programmer 16 may provide the processing intelligence to analyze the signals to populate the voiding log with voiding information. Wireless telemetry may be accomplished by radio frequency (RF) communication or proximal inductive interaction of sensor 86 with external programmer 24. In addition, wireless telemetry may follow Bluetooth protocols.

Power source 98 delivers operating power to the components of sensor 86. Power source 98 may include a small rechargeable or non-rechargeable battery and a power generation circuit to produce the operating power. Recharging may be accomplished through proximal inductive interaction between an external charger and an inductive charging coil within sensor 86. In some embodiments, power requirements may be small enough to allow sensor 86 to utilize patient motion and implement a kinetic energy-scavenging device to trickle charge a rechargeable battery. In other embodiments, power source 98 may employ a thermal energy scavenging device to store energy from the temperature gradient between the skin of patient 12 and the surrounding air. In alternative embodiments, traditional batteries may be used for a limited period of time.

In some embodiments, more complex characteristics may be used to detect voiding information such as deviation of a signal from an amplitude or frequency range, e.g., exceeding an upper threshold or falling below a lower threshold. Appropriate filter and amplifier circuitry, analog or digital, may be provided in the sensor or the processor to condition the signal so that such signal characteristics can be more specifically presented or isolated from extraneous information.

To detect voiding information sensing circuit 94 may determine whether the signal output by sensor 92 matches its requirements for voiding information. The signal output need not exactly match the corresponding requirements. Instead, a margin or difference threshold may be applied to indicate a voiding information if the sensor signal is within a given margin of the requirements. Again, the voiding information detection may be as simple as comparing sensor 92 signals to a threshold, e.g., to detect wetness. In more complex implementations, more detailed analysis of frequency and amplitude characteristics may be necessary to determine whether the sensor signal is sufficiently close to the requirements to define the output as voiding information.

As one example, processor 88 may generate a template signal corresponding to the requirement of voiding information and apply a correlation technique. In some embodiments, a single sensor signal may be correlated with not just one, but multiple signal features, such as amplitude, frequency, time intervals, and the like. In addition, correlation values for the individual signal features may be weighted with coefficients to prioritize some features over other features. The correlation values for the individual features may be summed to produce an overall correlation value, which may be compared to a threshold value to detect the voiding information.

Using a digital signal processor (DSP), for example, the processor captures a series of samples of sensor 92 output. For example, the samples may be captured continuously, but an average is taken over a certain number of samples. If the average of the sample signals satisfies the output requirements, then the voiding information is detected.

Figure 9:
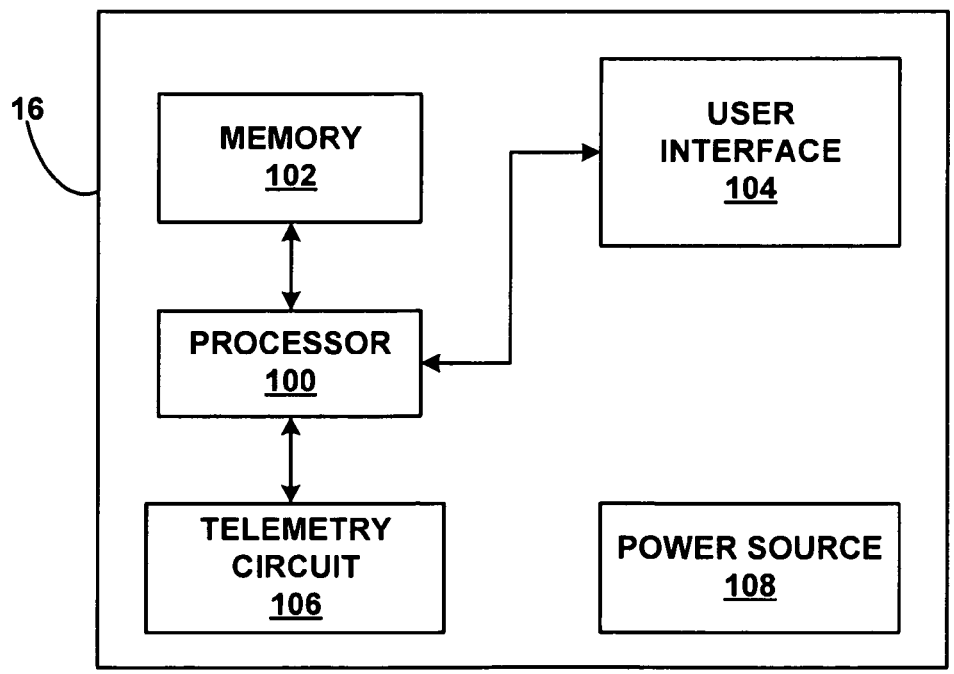
FIG. 9 is a functional block diagram illustrating various components of an external device that communicates wirelessly with a sensor.

FIG. 9 is a functional block diagram illustrating various components of an external device that communicates wirelessly with a sensor. As shown in FIG. 9, external programmer 16 includes processor 100, memory 102, telemetry circuit 106, user interface 104, and power source 108. The clinician or patient 12 interacts with user interface 104 in order to review the voiding log, modify a component of the voiding log, request voiding information from sensors 26, 42 or 68, or manually adjust one or more stimulation parameters of the stimulation therapy.

User interface may include a screen and one or more input buttons that allow external programmer 16 to receive input from a user. The screen may be a liquid crystal display (LCD), dot matrix display, or touch screen. The input buttons may include a touch pad, increase and decrease buttons, emergency shut off button, and other buttons needed to control the stimulation therapy. The clinician and patient 12 may review the voiding log of voiding information to determine an effective treatment or adjust currently delivered stimulation therapy.

Processor 100 controls user interface 104, retrieves data from memory 102 and stores data, such as voiding information, within the memory. Processor 100 also controls the transmission of voiding information through telemetry circuit 106 to stimulator 20 or sensors 26, 42 or 68. Memory 102 includes operation instructions for processor 100 and voiding information in a voiding log. In embodiments, where stimulation therapy is also delivered, memory 102 may also store stimulation parameters to define the therapy. Memory 102 may also include a history of all user inputs and changes to the voiding information for later review if necessary.

Telemetry circuit 106 allows the transfer of data to and from sensors 26, 42 or 68 and may also communicate with stimulator 20 if appropriate. Telemetry circuit 106 may receive voiding information automatically from sensors 26, 42 or 68 as one of the sensors detects voiding information, at a scheduled time, or when the telemetry circuit detects the proximity of one of the sensors. Alternatively, telemetry circuit 106 may communicate with sensors 26, 42 or 68 when requested by a user through user interface 104. Power source 108 may be a rechargeable battery, such as a lithium ion or nickel metal hydride battery. Other rechargeable or conventional batteries may also be used. In some cases, external programmer 16 may be used when coupled to an alternating current outlet.

Figure 10:
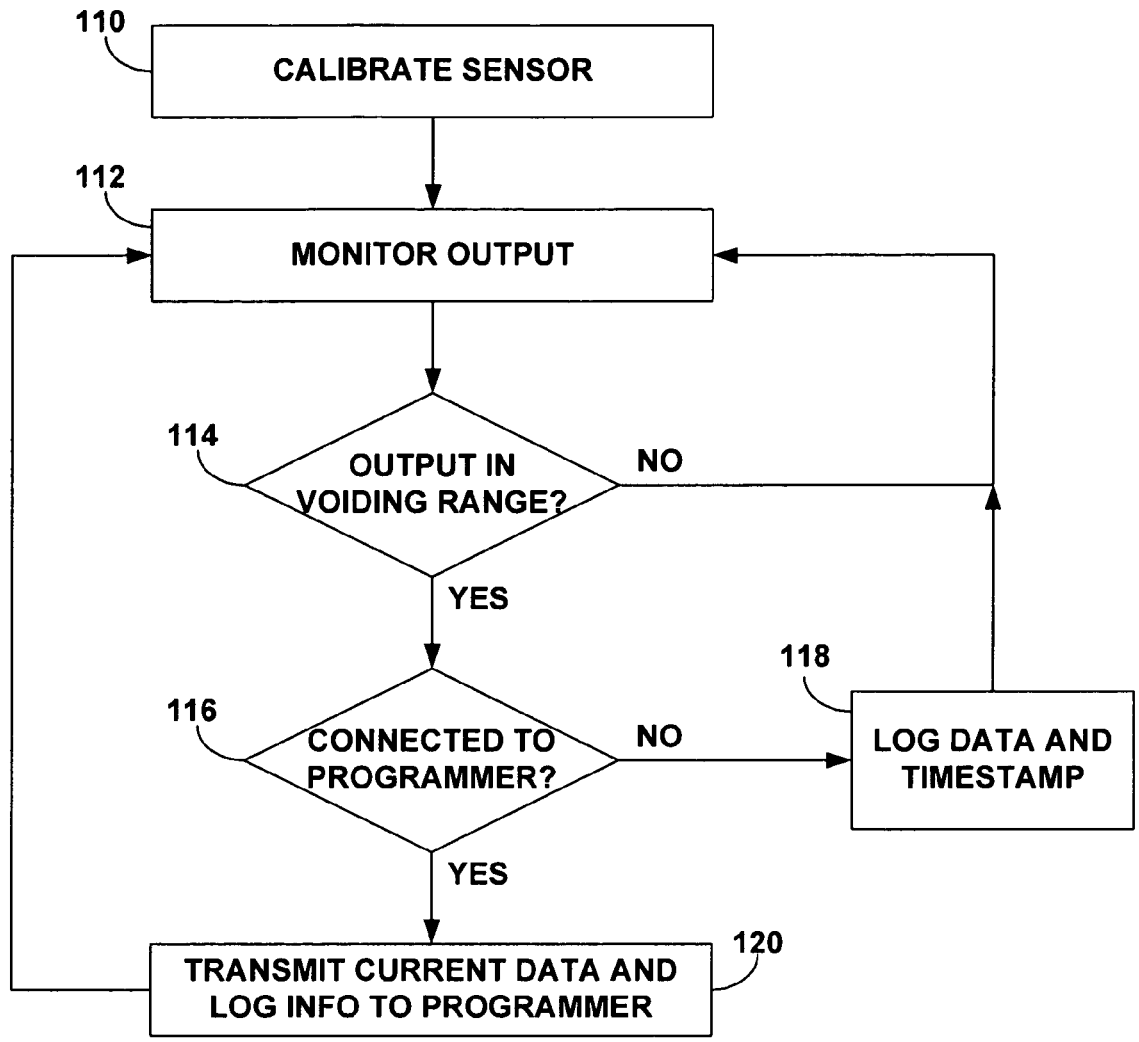
FIG. 10 is a flow chart illustrating a technique for detecting and storing voiding information, and transmitting a voiding log to an external device when connected to the sensor.

FIG. 10 is a flow chart illustrating a technique for detecting and storing voiding information, and transmitting a voiding log to an external device when connected to the sensor. As shown in FIG. 10, detecting voiding information begins by calibrating sensor 26 to non-voiding conditions (110). While other sensors may be used, sensor 26 is provided as an example herein. Sensor 26 monitors the output of sensing element 38 to detect voiding information from patient 12 (112). If the output is not within a voiding range, e.g., above a pre-determined threshold indicating wetness or some other parameter (114), sensor 26 continues to monitor the output (112).

If the output is within a voiding range (114), then sensor 26 checks to see if the sensor is connected to external programmer 16 (116). If sensor 26 is not connected to programmer 16, sensor 26 may log the voiding information in the voiding log locally and timestamps the information (118). The sensor then continues to monitor the output (112). If sensor 26 is connected to programmer 16, the sensor 26 transmits the current voiding information and any voiding log information to the programmer (120). Sensor 26 again continues to monitor output to detect voiding information (112). If communication with programmer 16 is possible, sensor 26 transmits available voiding log information including a current entry and any entries that have not previously been transmitted to the programmer.

In some embodiments, sensor 26 may directly store the voiding information in the voiding log of memory of the sensor before checking to see if there is a connection with external programmer 16. In any case, FIG. 10 illustrates the situation when sensor 26 attempts to continually send new voiding information as soon as possible. This technique may be used if the memory of sensor 26 is limited in size or patient 12 needs to constantly monitor the voiding log.

Figure 11:
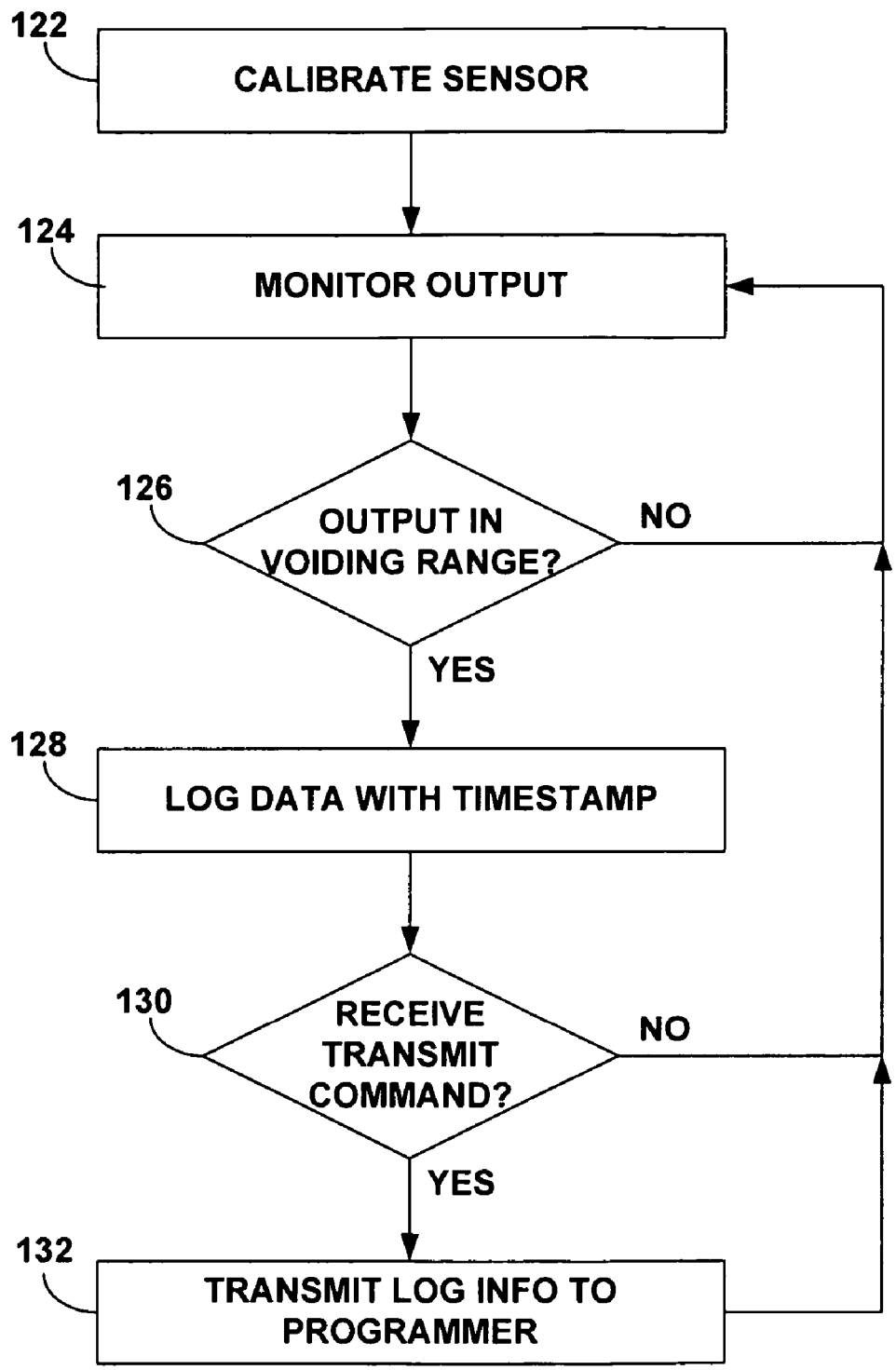
FIG. 11 is a flow chart illustrating a technique for detecting and storing voiding information, and transmitting a voiding log to an external device when requested by the device.

FIG. 11 is a flow chart illustrating a technique for detecting and storing voiding information, and transmitting a voiding log to an external device when requested by the device. As shown in FIG. 11, sensor 26 is used as an exemplary sensor to detect voiding information. The detection begins by initially calibrating sensor 26 according to the non-voiding environment (122). Sensor 26 continually monitors the output of sensing element 38 to detect any new voiding information from patient 12 (124). If sensor 26 determines that output is not within a pre-determined voiding range (126), sensor 26 continues to monitor the output (124).

If the output is within the voiding range (126), sensor 26 stores the output as voiding information in the voiding log and timestamps the information (128). If sensor 26 has not received a transmit command from external programmer 16 (130), sensor 26 continues to monitor the output (124). If sensor 26 has received a transmit command from programmer 16 (130), sensor 26 transmits the voiding log to the programmer (132). Sensor 26 subsequently monitors the output once more (124).

In some embodiments, sensor 26 may store all output from sensing element 38 as voiding information in the voiding log. In this case, the memory of sensor 26 may be capable of storing a large quantity of voiding information. The clinician may desire to review all data generated by sensor 26, not just voiding information as determined by the sensor. All the data may be reviewed in its entirety by the clinician on programmer 16, or the clinician may process the data offline at the programmer according to an arbitrary threshold to indicate which voiding information is indicative of a voiding event.

Figure 12:
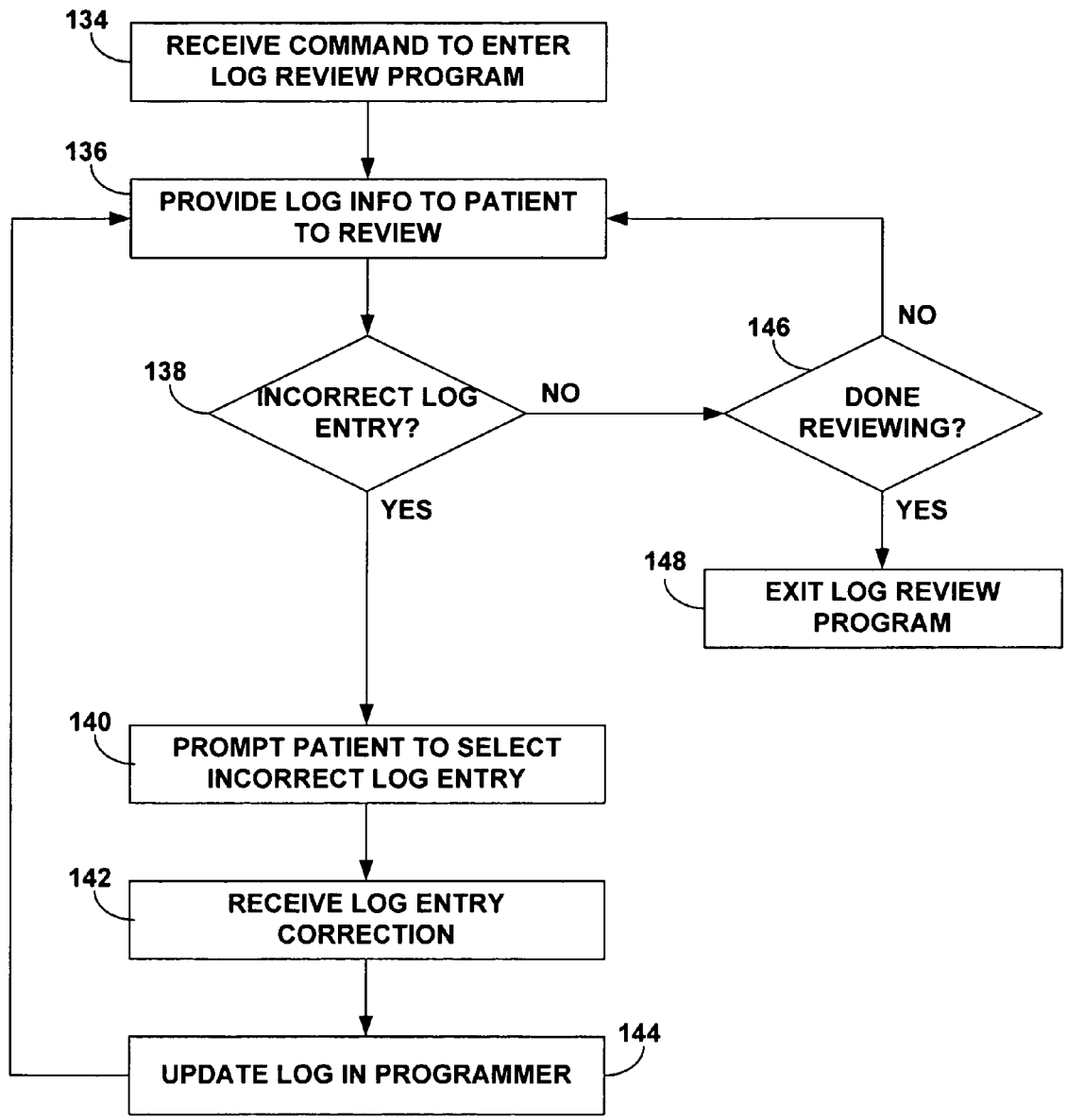
FIG. 12 is a flow chart illustrating a technique for reviewing and correcting voiding information in a voiding log.

FIG. 12 is a flow chart illustrating a technique for reviewing and correcting voiding information in a voiding log. As shown in FIG. 12, external programmer 16 already has received the voiding log from sensor 26 and receives a command from a user to enter the log review program (134). Programmer 16 subsequently retrieves the voiding log from the memory and provides the voiding information to patient 14, or another user, to review via user interface 104 (136). Patient 12 reviews the voiding log and looks to identify any incorrect voiding information, or log entry (138).

If patient 12 identifies any incorrect entry, programmer 16 prompts the patient to select the incorrect entry to correction (140). Programmer 16 subsequently receives an input from patient 12 that corrects the log entry and the voiding information (142). Programmer 16 then updates the voiding log stored in the programmer with the modified voiding information (144), and the programmer again provides the voiding log to patient 12 for review (136).

If patient 12 does not identify an incorrect entry, programmer 16 prompts the patient to decide if the patient is done reviewing the voiding log (146). Programmer 16 again provides the voiding log to patient 12 if the patient is not done reviewing the log. If patient 12 has determined that the review has been completed, programmer 16 exits the log review program and returns to a main operating screen (148).

In some embodiments, external programmer 16 may only allow the clinician to modify voiding information in the voiding log. The clinician may lock the log review program with a password to prevent patient 12 from corrupting the voiding log. Alternatively, the clinician may even remove the log review program from programmer 16 during patient 12 use to further prevent voiding log corruption. In other embodiments, programmer 16 may allow patient 12 to review the voiding log or voiding information in real-time during voiding detection. External programmer 16 may signal patient 12 via an audible ring or vibrating notification to confirm the detected voiding event. The clinician may also direct this real-time confirmation of voiding events.

Figure 13:
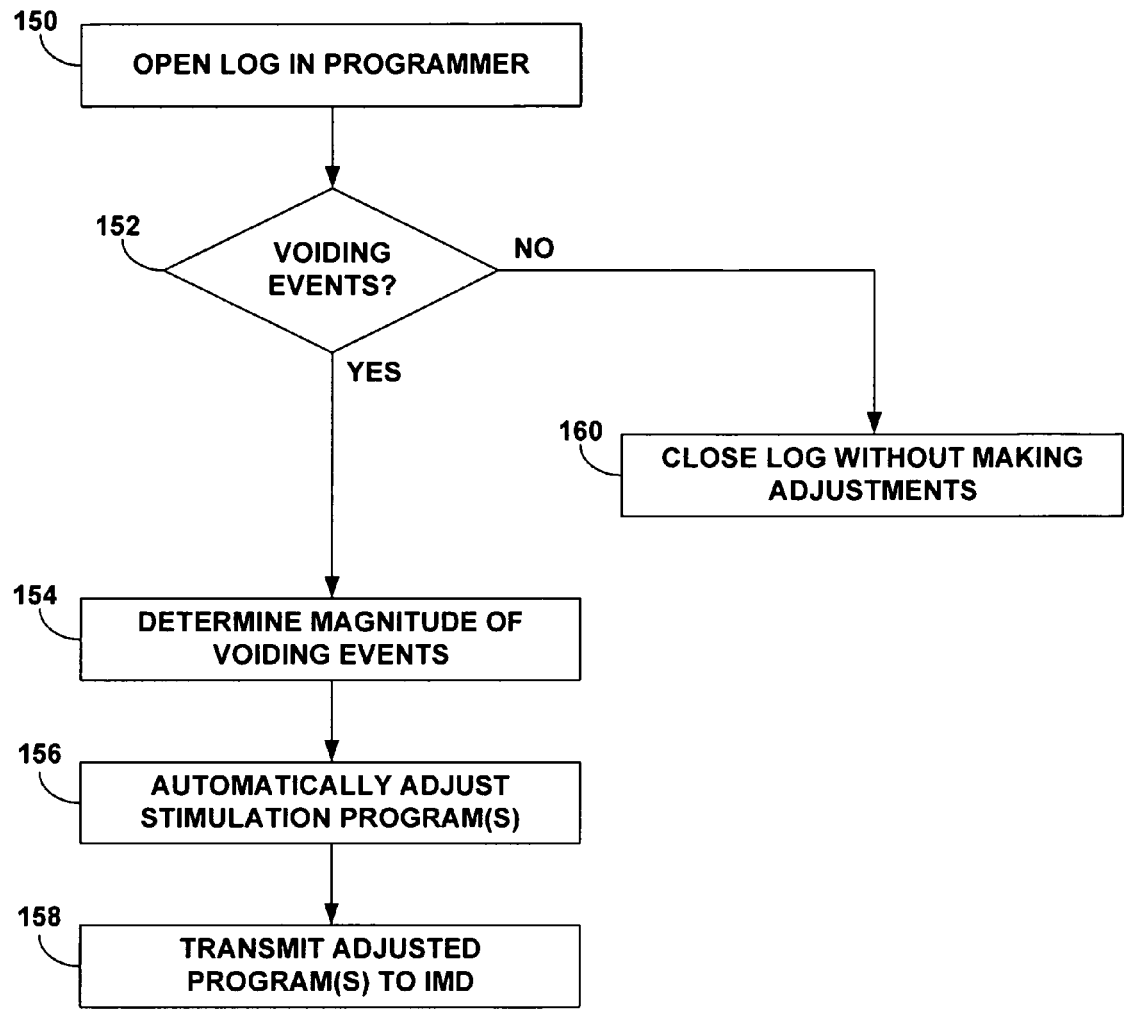
FIG. 13 is a flow chart illustrating a technique for automatically adjusting stimulation therapy with the voiding information in the voiding log.

FIG. 13 is a flow chart illustrating a technique for automatically adjusting stimulation therapy with the voiding information in the voiding log. As shown in FIG. 13, processor 100 begins the automatic adjustment process by opening the voiding log in programmer 16 (150). Processor 100 processes the voiding log and identifies any voiding events (152). If processor 100 does not identify any voiding events, there is no feedback to make stimulation adjustments, and the processor closes the voiding log without modifying a single stimulation parameter of the therapy (160).

If processor 100 identifies any voiding events in the voiding information, the processor determines the magnitude of the voiding events (154). The magnitude of a voiding event may be the duration of the event, the frequency of leakage (i.e., number of leakage events per unit time such as day, week or month), the amount of urine voided, and/or other information characterizing the voiding event beyond simply detecting an event. Processor 100 uses the voiding information to automatically adjust one or more stimulation parameters, such as amplitude, pulse width or pulse rate, of one or more stimulation programs that were used to deliver therapy during the voiding event (156). The automatic adjustment may be governed by a set of rules or instruction of memory 102 within programmer 16. Programmer 16 subsequently transmits the one or more adjusted programs to stimulation 20, e.g. an implantable medical device (IMD), for improved stimulation therapy.

The techniques described in this disclosure may be implemented in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry.

When implemented in software, the functionality ascribed to the systems and devices described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic media, optical media, or the like. The instructions are executed to support one or more aspects of the functionality described in this disclosure Many embodiments of the invention have been described. Various modifications may be made without departing from the scope of the claims. For example, although the invention has been generally described in conjunction with external sensors of an undergarment, sensors located elsewhere on patient 12 may be used in conjunction within an external programmer or even an implanted stimulator. In addition, other implantable medical devices, such as electrical muscle stimulation devices, functional electrical stimulation (FES) devices, and implantable drug delivery devices, each of which may be configured to treat incontinence or other conditions or disorders, may be used. These and other embodiments are within the scope of the following claims.

The invention claimed is:

1. A method comprising:
   detecting urinary voiding information via a sensor disposed adjacent to a patient via an undergarment worn by the patient;
   storing the voiding information in a voiding log;
   delivering electrical stimulation therapy to the patient according to a set of stimulation parameters to alleviate urinary incontinence; and
   adjusting one or more of the stimulation parameters based on the voiding information in the voiding log.

2. The method of claim 1, wherein storing the voiding information in a voiding log includes locally storing the voiding information in a voiding log in memory associated with the sensor.

3. The method of claim 1, wherein storing the voiding information in a voiding log includes transmitting the voiding information to an external device for storage in a voiding log in memory associated with the external device.

4. The method of claim 1, further comprising displaying the voiding information in the voiding log to a user.

5. The method of claim 4, further comprising receiving user input correcting the voiding information.

6. The method of claim 1, wherein detecting voiding information comprises detecting voiding of urine from the patient.

7. The method of claim 6, further comprising identifying a characteristic of the urine, wherein the characteristic is at least one of an impedance, a temperature, a pH, a volume, and an electrolyte concentration.

8. The method of claim 1, wherein detecting voiding information comprises detecting deformation of at least a portion of the undergarment, wherein the deformation indicates that the patient has removed the undergarment to voluntarily void urine.

9. The method of claim 1, wherein adjusting one or more of the stimulation parameters includes adjusting one or more of the stimulation parameters in response to user input based on review of the voiding information in the voiding log.

10. The method of claim 1, wherein adjusting one or more of the stimulation parameters includes automatically adjusting one or more of the stimulation parameters based the voiding information in the voiding log.

11. The method of claim 1, further comprising transmitting the voiding information from the sensor to an external device via wireless telemetry.

12. A system comprising:
    an undergarment for a patient;
    a sensor carried by the undergarment and positioned to detect urinary voiding information;
    a memory that stores the voiding information in a voiding log;
    an implantable stimulator that delivers electrical stimulation therapy according to a set of stimulation parameters to the patient to alleviate urinary incontinence; and
    a processor that adjusts one or more stimulation parameters based on the voiding information in the voiding log.

13. The system of claim 12, wherein the memory storing the voiding log resides within the sensor.

14. The system of claim 12, further comprising an external device, wherein the memory storing the voiding log resides within the external device, and the sensor includes telemetry circuitry to transmit the voiding information to the external device.

15. The system of claim 12, further comprising an external device that receives the voiding information in the voiding log from the sensor and displays the voiding information in the voiding log to a user.

16. The system of claim 12, further comprising an external device that receives the voiding information in the voiding log from the sensor, wherein the external device receives user input correcting the voiding information.

17. The system of claim 12, wherein the sensor detects voiding of urine from the patient as at least part of the voiding information.

18. The system of claim 17, wherein the sensor identifies a characteristic of the urine, wherein the characteristic is at least one of an impedance, a temperature, a pH, a volume, and an electrolyte concentration.

19. The system of claim 12, wherein the sensor detects deformation of at least a portion of the undergarment as at least part of the voiding information, the deformation indicating that the patient has removed the undergarment to voluntarily void urine.

20. The system of claim 12, further comprising
    an external programmer that comprises the processor that adjusts the one or more of the stimulation parameters based on the voiding information in the voiding log.

21. The system of claim 12, wherein the processor adjusts the one or more of the stimulation parameters in response to user input based on review of the voiding information in the voiding log.

22. The system of claim 12, wherein the processor automatically adjusts the one or more of the stimulation parameters based the voiding information in the voiding log.

23. The system of claim 12, further comprising transmitting the voiding information from the sensor to an external device via wireless telemetry.

24. A system comprising:
   means for detecting urinary voiding information via a sensor disposed adjacent to a patient via an undergarment worn by the patient;
   means for storing the voiding information in a voiding log;
   means for delivering electrical stimulation therapy according to a set of stimulation parameters to the patient to alleviate urinary incontinence; and
   means for adjusting one or more of the stimulation parameters based on the voiding information in the voiding log.

25. The system of claim 24, further comprising means for locally storing the voiding information in a voiding log in memory associated with the sensor.

26. The system of claim 24, further comprising means for transmitting the voiding information to an external device for storage in a voiding log in memory associated with the external device.

27. The system of claim 24, wherein the means for detecting voiding information detects voiding of urine from the patient.

28. A system comprising:
   an implantable stimulator that delivers electrical stimulation therapy to a patient to alleviate urinary incontinence;
   an undergarment for the patient;
   a sensor carried by the undergarment and positioned to detect urinary voiding information;
   an external programmer that controls the implantable stimulator and receives the voiding information from the sensor, wherein the programmer stores the voiding information in a voiding log; and
   a processor that adjusts the electrical stimulation therapy based on the voiding information in the voiding log.

29. The system of claim 28, wherein the external programmer displays the voiding information in the voiding log to a user, and receives user input correcting the voiding information.

30. The system of claim 28, wherein the external programmer comprises the processor that adjusts the electrical stimulation therapy based on the voiding information in the voiding log.

31. The system of claim 28, wherein the processor adjusts the electrical stimulation therapy in response to user input based on review of the voiding information in the voiding log.

32. The system of claim 28, wherein the processor automatically adjusts the electrical stimulation therapy based the voiding information in the voiding log.

* * * * *